United States Patent [19]

Munk

[11] Patent Number: 5,147,668
[45] Date of Patent: Sep. 15, 1992

[54] PROCESS OF PRODUCING A RECONSTITUTABLE SOLID LACTIC ACID DRIED PRODUCT

[76] Inventor: Werner G. Munk, Bergstr. 12,, D-7981 Vogt/Ravensburg, Fed. Rep. of Germany

[21] Appl. No.: 577,793

[22] Filed: Sep. 5, 1990

Related U.S. Application Data

[63] Continuation of Ser. No. 234,256, Aug. 19, 1988, abandoned.

[30] Foreign Application Priority Data

Aug. 21, 1987 [DE] Fed. Rep. of Germany ....... 3727946

[51] Int. Cl.$^5$ .................. A23C 9/12; A23B 7/024
[52] U.S. Cl. ..................... 426/61; 426/71; 426/317; 426/524; 426/580; 426/583
[58] Field of Search ............ 426/580, 583, 524, 61, 426/71, 317

[56] References Cited

U.S. PATENT DOCUMENTS

| | | | |
|---|---|---|---|
| 4,187,321 | 2/1980 | Mutai et al. | 426/43 |
| 4,396,631 | 8/1983 | Adachi et al. | 426/61 |
| 4,797,290 | 1/1989 | Tukumaru et al. | 426/43 |

FOREIGN PATENT DOCUMENTS

1284822  9/1970  United Kingdom.

OTHER PUBLICATIONS

Rasic, J. and Kurmann, J., Bifidobacteria and their Role, 1983, pp. 138-143.

*Primary Examiner*—Jeanette Hunter
*Assistant Examiner*—Helen Pratt
*Attorney, Agent, or Firm*—Ostrolenk, Faber, Gerb & Soffen

[57] ABSTRACT

A process for preparing a solid dried product which is reconstitutable by saliva and storable at room temperature, is described. The product has a lactulose content of below 0.5% by weight (based on the dried product), carbohydrates, lactic acid bacteria, and optionally further additives. The lactic acid bacteria content is at least $10^8$/g of substance. Various uses of the product are described, including its use as a pharmaceutical preparation, a dietetic product, an addition to foods, a food or food additive for animals, or a semi-finished product or slimming diet product swellable in the mouth.

8 Claims, 2 Drawing Sheets

PROCESS OF PRODUCING A RECONSTITUTABLE SOLID LACTIC ACID DRIED PRODUCT

This is a continuation of application Ser. No. 07/234,256, filed on Aug. 19, 1988, now abandoned.

This invention relates to a solid dried product reconstitutable by saliva and storable at room temperature, having a lactulose content of below 0.5% by weight, based on the dried product, for direct consumption on the basis of milk or milk products and a content of lactic acid bacteria, a process for the production thereof and its use.

The lactic acid bacteria, i.e. anaerobic bacteria, which secrete lactic acid (lactate) as the main end product in the carbohydrate catabolism, represent an essential component of the intestinal flora. It is particularly important that the population of the bifidus bacteria belonging to the lactic acid bacteria is available in the intestine in sufficient quantity. The bifidus bacteria are supplied to the large intestine of babies with mother's milk, and already in babies a strong and anti-infectious bifidus flora develops in the intestine. It has been known that the intestinal flora may be disordered and damaged by numerous external influences. Disorders of the intestinal flora may result, for example, from antibiotics, sulphonamides, antidiabetics and irradiation. The intestinal flora is also disordered in the case of indigestions resulting from ferments and bacteria, intestinal intoxications and their sequels. Thus, there exists a need for agents by which the disordered and/or damaged intestinal flora can be rendered intact again.

Also in healthy people it is favorable to regenerate and renew the population of lactic acid bacteria, especially bifidus bacteria, in the intestine. If preparations helping to influence the lactic acid bacteria concentration in the intestine are administered orally, it will be required for the preparations to overcome the stomach passage. The lactic acid cultures disintegrate in the stomach and in order to achieve a certain lactic acid bacteria concentration in the intestine, the lactic acid bacteria, especially bifidus bacteria, concentration has to be as high as possible.

Lactic acid bacteria are present in foods or beverages obtained from plants such as, for example, sauerkraut, wine and beer and in milk and milk products such as, for example, butter, cheese, buttermilk and yoghurt. Among these products the consumption of milk and milk products, especially buttermilk and yoghurt has increased considerably in the past few years, since the health consciousness of the people has increased. The consumption of yoghurt has multiplied in the past few years.

Lactic acid forming bacteria are usually preserved by cooling or deep-freezing or in a dry state as a spray-dried or freeze-dried product which can be added to foods or pharmaceutical preparations, which are not heated to a temperature fatal e.g. to bifidus bacteria, i.e. they are admixed just before being consumed.

Various products have been known, which contain lactic acid bacteria and are used for treating disorders of the intestinal flora resulting from damage due to antibiotics, sulphonamides, antidiabetics and irradiation, indigestions due to ferments and bacteria and their sequels. The commercially available products, however, have various disadvantages. Some of the known products cannot be stored at room temperature. However, the most essential disadvantage of the known products is that the concentration of lactic acid bacteria is too low. Only part of the lactic acid bacteria passes through the stomach, and the concentration of the lactic acid bacteria achieved in the intestine is not high enough. Another disadvantage is that part of the known products contains additives for preservation. Lactic acid forming bacteria are usually preserved by cooling or deep-freezing.

EP-A-9 219 sets forth dry chip-like slices of food or luxury food and processes for their production. On account of their shape and consistency these known products are suitable for immediate consumption. They are produced in that an aqueous basic substance of food raw materials, which contains water-soluble and water-insoluble builder substances, optionally accompanied by the addition of flavoring agents and spices, is prepared so as to give a composition ready to be consumed, which shows a still flowable viscous to plastically deformable consistency. The composition is shaped into slices having a thickness of from 1 to 10 mm and then carefully dried accompanied by the formation of a porous dried product. The drying process carried out is vacuum-drying or freeze-drying at a temperature of up to a maximum of 65° C.

The known composition can be produced from a basic substance consisting of milk products and may contain yoghurt cultures. The disadvantage of the known chip-shaped product produced from such a basic substance is that the concentration of lactic acid bacteria is about $10^5$/g. This concentration is not satisfactory.

DE-OS 31 32 563 sets forth a process for the production of freeze-dried products, especially foods, in which the products obtain a freeze-dryable form prior to freeze-drying and are pre-frozen by cooling with liquid nitrogen. The gaseous nitrogen can simultaneously be used as a sweep gas for portioning and freeze-drying. If this known process is used for the production of freeze-dried products consisting of milk or milk products such as, for example, yoghurt, products will be obtained, whose lactic acid bacteria concentration is not high enough.

DE-PS 27 55 037 C2 sets forth a powdery agent containing 28 to 57% by weight of lactulose and at least $8 \times 10^{10}$ of freeze-dried microorganism cells belonging to the genus of bifidus bacteria. According to this citation the viability of the bifidus bacteria is increased by the lactulose content. The disadvantage of this product is that lactulose is virtually to be admixed to this product as an inert substance and that it is only available as a powdery agent. When used the powdery agent has to be dissolved and/or suspended in water. The disadvantage of this known product is that it is not suited for immediate consumption but has to be dissolved and/or suspended in water beforehand. Another disadvantage thereof is that it is required to store the powdery product at a cool and dark place, since the mixture has a high degree of hygroscopicity. Therefore, the powdery product has to be packed airtight or filled in capsules and then packed airtight before it is sold.

It is the object of the present invention to provide a solid dried product for direct consumption, i.e. not a powdery dried product, on the basis of milk or milk products, which has a high content of lactic acid bacteria, especially bifidus bacteria. The lactic acid bacteria are to have the capacity of resuscitation and population. The product is to be reconstitutable by the saliva. It is to be storable at room temperature for at least three months, without the content of lactic acid bacteria substantially changing. The product is not to contain admixed lactulose. The content of lactulose is to be below 0.5% by weight, based on the product.

A product is to be provided according to the invention, which can also be used as a culture and/or semifinished product for the production of yoghurt. The product according to the invention is to be used as food, pharmaceutical preparation, dietetic or as a food additive. Furthermore, it is to be used as food or food additive for animals.

Furthermore, a process for its production is to be provided, which can easily be carried out.

Figure 1A:
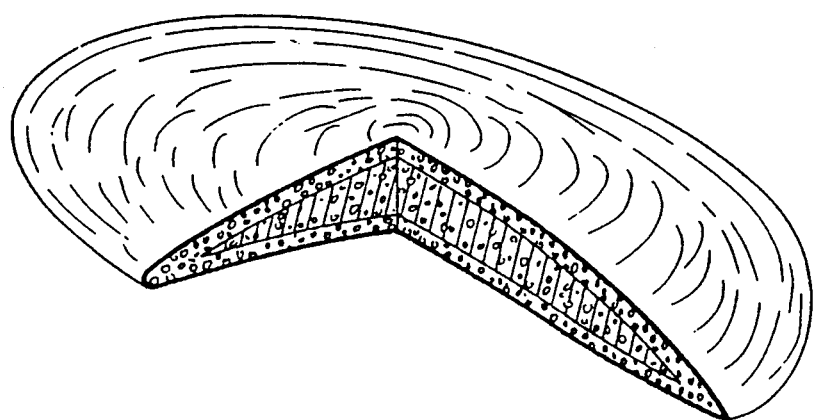
FIG. 1A shows a solid porous product according to the invention.

The subject matter of the invention is a product of the type mentioned in the beginning, which is characterized in that the content of lactic acid bacteria amounts to at least $10^8$/g of substance.

The content of lactic acid bacteria is preferably within a range of from $10^8$/g to $10^{12}$/g, particularly preferably within a range of from $10^9$/g to $10^{10}$/g.

After storage at room temperature for at least three months, a particularly preferred product according to the invention has a content of lactic acid bacteria within a range of from $10^8$/g to $10^{10}$/g, particularly preferably of at least $10^9$/g.

The product according to the invention is available in the shape of slices, chips, small rods, figures and optionally provided with a coat e.g. of sugar, chocolate, etc.

Furthermore, the invention relates to a process for the production of the product by preparing an aqueous basic mixture on the basis of milk and/or milk products, carbohydrates and optionally further additives, homogenization, heating, cooling, inoculation, incubation, and ultrafast freezing by means of liquid nitrogen, which is characterized in that the mixture is flow molded in the presence of an inert gas atmosphere, the molded product is frozen ultrafast or by cryotransfer in the presence of an inert gas atmosphere, the frozen product is collected in the presence of an inert gas atmosphere, optionally put in intermediate storage in the presence of an inert gas atmosphere, freeze-dried in the presence of an inert gas atmosphere, and packed gas and aroma-tight in the presence of an inert gas atmosphere.

Nitrogen is preferably used as the inert gas in all stages, since the nitrogen applied for cryotransfer may be used for the molding, freeze-drying and packaging stages. However, it is also possible to use other inert gases. Ultrafast freezing is carried out such that the product reaches a core temperature of at least $-15°$ C., preferably a core temperature within the range of between $-15°$ C. and $-50°$ C. Intermediate storage may but does not have to be carried out. This is done when the freeze-drying apparatus is still occupied. Intermediate storage is carried out at a temperature within the range of between $-15°$ C. and $-50°$ C. Freeze-drying takes place at a pressure within the range of between 0.1 and 50 mbar, preferably at a pressure within the range of between 1 and 5 mbar, and at a temperature preventing the product temperature from exceeding $+45°$ C. In the case of the process according to the invention it is essential that a product temperature of $+45°$ C. is not exceeded. The residual water content should be <5%, optimally 2 to 3%, at the end of drying.

For optimum storage the dried product is packed in preferably aluminum-coated polypropylene sheet in the presence of a nitrogen atmosphere. It is essential to pack the product according to the invention gas and/or aroma-tight in a material impervious to light.

The milk or milk products used may be milk of all fat contents, milk concentrates such as concentrated skimmed milk or full-cream milk, products enriched with soybean protein such as soybean milk, and milk-like nutrition media.

Examples of carbohydrates are sugars, especially crystallizable sugars such as glucose, sucrose, fructose, lactose, sugar substitutes such as sugar alcohol, starch and starch products including starch decomposition products, grains and cereals, respectively, in chopped form, vegetables such as fruit, nuts and suitable greens as well as their prepared forms. The product according to the invention does not contain lactulose or only contains lactulose within a range of between 40 and 100 ppm. In other words, the product according to the invention is free of lactulose or contains little lactulose.

According to the invention the product contains lactic acid bacteria. It preferably contains microorganisms belonging to the genus of bifidus bacteria which are counted among the lactic acid bacteria.

The additives used may be all of the additives presently used in the field of foods. Examples are thickening agents, emulsifiers, foam stabilizing agents, aromatics, coloring and flavoring agents, mineral substances and trace elements.

It was surprising and not obvious that a product is obtained by ultrafast freezing with liquid nitrogen and operating in the presence of an inert gas atmosphere, which maintains a lactic acid bacteria concentration within the range of from $10^8$/g to $10^{10}$/g after storage at room temperature for at least three months. The products produced according to the process of the invention have the property of not loosing their nutrition-physiologically properties over a prolonged period of storage. The lactic acid bacteria contained in the product remain viable and reproducible in highly concentrated form over a period of weeks or months, serve the purpose of natural enrichment of the intestinal flora but also supplementation when consuming heat-treated (preserved) milk products.

According to the process of the invention products are preferably produced in the shape of chips, reference being made expressis verbis to the disclosure of EP-A-9 219 and DE-OS 31 32 563. The advantage of chips is that a chip ($\approx 1$ g) contains a portion of bifidus bacteria capable of resuscitation and population at least the same as contained in a 100 g cup of commercially available yoghurt with detectable bifidus bacterium.

Due to the low own weight and the high swelling capacity and a high increase in volume in combination with the saliva a feeling of satiety is obtained with a 1 g chip nearly the same as is obtained with the consumption of 100 g of fresh yoghurt. During mastication the salivation is increased stimulated by the melting process of the fine-pored structure of the dried product. Thus, with low supply of calories an effect is obtained making the product perfect for a slimming diet.

The first step of chip production is the same as that of yoghurt except for the enrichment of the dry substance necessary for freeze-drying, i.e. heating milk, skimmed milk powder and sugar, cooling to incubation temperature, inoculating with bifidus-containing yoghurt culture, incubating to the desired pH value (preferably 4.9) and portioning for freeze-drying by flow molding described in the enclosure subsequently to cooling (+4° C.).

Freeze-drying is to be carried out such that the product surface temperature does not exceed the maximum incubation temperature of the bacterium to be dried in order to keep it alive.

The thus produced yoghurt chips with a maximum height of 10 mm, preferably 2 to 5 mm, and a diameter of preferably 20 to 30 mm have a dry weight of about 1 g and contain at least $1 \times 10^{10}$ of detectable bifidus bacteria per gram, which reduced to $1 \times 10^9/g$ after three-month storage at room temperature. The capacity of resuscitation and population of the yoghurt bacteria can be detected in that the freeze-dried chips may be used as a "culture" for the production of yoghurt.

Fresh yoghurt with detectable bifidus bacteria contains an average of $1 \times 10^5$ of detectable bifidus bacteria per g after three-week storage at +8° C. to +10° C., i.e. a bifidus yoghurt chip contains at least 10,000 times the amount of bifidus bacteria as compared to one gram or at least 100 times the amount thereof as compared to a 100 g cup of fresh yoghurt. In order to consume the amount of bifidus bacteria the same as is contained in 5 yoghurt chips (1 g each) per day thus at least 500 cups (100 g each) of fresh yoghurt would have to be consumed per day.

The products prepared according to the process of the invention have the property of not loosing their nutrition-physiological properties over a prolonged period of storage. The lactic acid bacteria contained in the product remain viable and reproducible in highly concentrated form over a period of weeks or months, serve the purpose of natural enrichment of the intestinal flora but also supplementation when consuming heat-treated (preserved) milk products. The invention is explained in detail by means of the enclosed drawings.

FIG. 1A shows a solid porous product according to the invention and

Figure 1B:
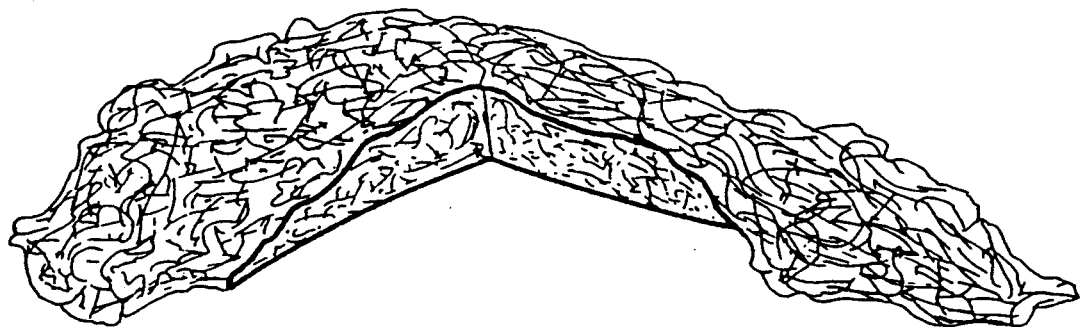
FIG. 1B shows a prior art (loose, powdery) product.

FIG. 1B shows the loose powdery known product.

It is assumed that the thermostorable preservation of the bacteria is achieved by the fine-pored structure, since this fine-pored structure serves as a "protecting wall".

As in the case of spray-dried powder, the bacteria embedded with the surface pores are damaged by external influences during thermal storage thereby, however, forming an effective protective shield for the bacteria embedded in the pore system.

Due to this protective effect the bacteria in the interior of the chip remain viable and reproducible at room temperature for a period of time far longer as compared to the spray-dried powder, i.e. as compared to the powder the present concentration of bacteria only decreases by the power of ten, in this case from $10^{10}$ to $10^9/g$, after e.g. three months, while the concentration of commercially available powdery products is reduced to a greater extent.

Figure 2:
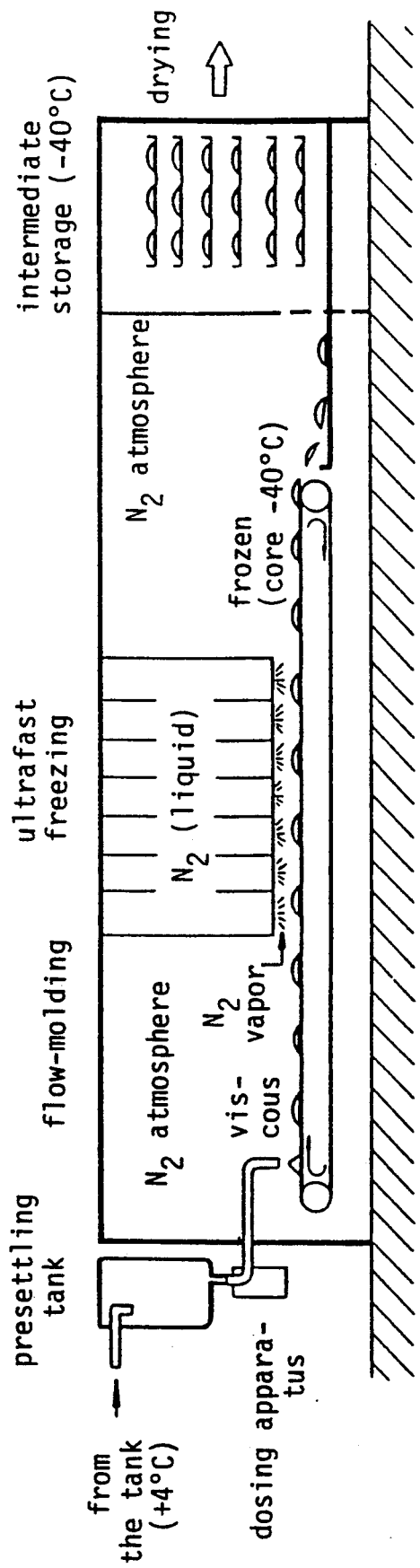
FIG. 2 shows a schematic diagram of the flow molding according to the invention accompanied by ultrafast freezing.

FIG. 2 shows a schematic diagram of the flow molding according to the invention accompanied by ultrafast freezing.

The basic substance is fed from a tank to a presettling tank. In the presence of an $N_2$ atmosphere the composition is portioned onto a continuous belt by a dosing apparatus. The individual portioned parts are subjected to ultrafast freezing by means of liquid nitrogen and supplied to freeze-drying in the presence of an $N_2$ atmosphere, optionally after intermediate storage.

The products produced according to the invention are used as a food additive, as pharmaceutical preparations, dietetics, for human beings and animals as well as food or food additive and as semi-finished product for the preparation of yoghurt as well as a slimming diet swellable in the mouth.

In the following, the preparation of natural yoghurt slices containing dextrose is explained in general.

NATURAL YOGHURT SLICES CONTAINING DEXTROSE

General prescription:

| | |
|---|---|
| full-cream milk 3.5% of fat | 77% |
| skimmed milk powder | 9% |
| dextrose | 8% |
| starch | 1% |
| active yoghurt culture | 5% |

Production:
stirring skimmed milk powder, dextrose and starch into cold milk;
heating to +130° C./s (with pre-homogenization 200 bar at +60° C.);
cooling to +45° C.;
inoculation (addition of bifidus-containing culture, mixing);
incubation at +43° C. (up to 1.5% of lactic acid, pH about 4.9);
cooling to +4° C. (by stirring);
shaping after flow molding;
intermediate storage (if necessary);
freeze-drying;
packaging.

The following examples explain the invention i.e., a solid, dried product reconstitutable by saliva and storable at room temperature, having a lactulose content of below 0.5% by weight, based upon the dried product, and a content of lactic acid bacteria of at least $10^8/g$ of substance, for direct consumption.

EXAMPLE 1

NATRUAL YOGHURT SLICES CONTAINING DEXTROSE

A dried mixture consisting of 11.7 kg of skimmed milk powder, 10:4 kg of dextrose and 1.3 kg of starch is slowly added by stirring into 100 kg of cold full-cream milk (3.5% of fat). The preparation is preheated to +60° C., homogenized at this temperature with 200 bar, shortly heated to +130° C., cooled to +45° C., 6.5 kg of bifidus-containing culture are added to the flowing stream and supplied to an incubation tank containing a nitrogen atmosphere, whereby the nitrogen atmosphere displaced by the supplied preparation can escape through a sterilisation filter and a minor nitrogen excess pressure for anaerobic incubation results in the top space of the incubation tank.

After incubation at +43° C. up to a lactic acid content of 1.5% ($\approx$pH about 4.9), it is cooled to +4° C. by stirring, in the presence of a nitrogen atmosphere: flow-molded, ultrafast frozen, if necessary put in intermediate storage and packed in the presence of nitrogen after freeze-drying.

EXAMPLE 2

NATURAL YOGHURT SLICES CONTAINING FRUCTOSE 1.5 kg of skimmed milk powder (free of inhibitors) are thoroughly mixed with 1 kg of fructose and 200 g of gelatin and slowly added by stirring into 6 kg of water.

This preparation is heated to +95° C. in a steamer and kept at this temperature for 30 minutes.

After cooling to +37° C. (in the iced water bath by stirring) the preparation is inoculated with 1.5 kg of bifidus-containing culture and incubated at +37° C. to a pH value of 4.6, then cooled in the iced water bath to <+10° C.

After the inoculation the top space of the incubation tank has to be swept with inert gas to displace the oxygen.

After cooling the yoghurt composition is smoothed by vigorous stirring and cooled to ±0° C. (avoid incorporation of air).

The cooled composition is applied to a prefrozen sheet (at least −40° C.) in 5 ml portions by means of a sterile pipette, thereby allowing it to expand in slice shape.

After subsequent deep-freezing at −55° C. over a period of 24 hours freeze-drying is carried out at <2 mbar and a maximum of +35° C.

EXAMPLE 3

Milk Chips I

A skimmed milk concentrate having a dry substance content of about 27% (≃triple concentration) is inoculated with 20% of bifidus-containing culture and incubated in the presence of a nitrogen atmosphere at +36° C. up to a pH value=4.9.

The soured composition is cooled in the presence of a nitrogen atmosphere and smoothed by stirring, then flow-molded, frozen and freeze-dried.

EXAMPLE 4

It is operated as set forth in Example 3 and the skimmed milk concentrate is replaced by a full-cream milk concentrate having a dry substance content of 40%.

EXAMPLE 5

Milk Chips II 10 kg of shortly heated milk are mixed with 0.8 kg of bifidus-containing yoghurt culture at +37° C. and incubated anaerobically (in the absence of air) at +37° C. up to a pH of 4.6.

The viscous composition is concentrated by dehydration at +35° C. in the vacuum rotational vaporizer to yield a dry substance content of 30 to 40%, then processed by flow-molding, freezing and freeze-drying as set forth in Example 1 to obtain the final product.

I claim:

1. A process for the production of a solid, dried product for direct consumption which is reconstitutable by saliva and storable at room temperature, consisting essentially of milk or a milk product, carbohydrates, lactic acid bacteria in an amount of at least about $10^8/g$ of the dried product and lactulose in an amount below about 0.5% by weight based upon the weight of the dried product, said product containing an outer portion comprising a fine-pore structure for protecting the lactic acid bacteria contained within the product such that lactic acid bacteria within the product remains viable for a prolonged period of storage, comprising the steps of:

(a) preparing an aqueous basic mixture of milk or milk product and carbohydrates,
   (b) homogenizing the mixture,
   (c) heating the mixture,
   (d) cooling the mixture,
   (e) inoculating the mixture with lactic acid bacteria,
   (f) incubating the mixture in the presence of an inert gas atmosphere,
   (g) flow-molding the mixture to produce a flow-molded product,
   (h) ultrafast freezing the flow-molded product in the presence of an inert gas atmosphere,
   (i) collecting the frozen product in the presence of an inert gas atmosphere,
   (j) freeze-drying the frozen product in the presence of an inert gas atmosphere, and
   (k) packing the dried product in a gas and aroma tight packaging in the presence of an inert gas atmosphere.

2. The process according to claim 1, wherein the ultrafast freezing comprises cryotransfer.

3. The process according to claim 1, wherein nitrogen is used as the inert gas in all stages.

4. The process according to claim 1, wherein the ultrafast freezing is carried out such that the product reaches a core temperature of at least −15° C.

5. The process according to claim 1, wherein the ultrafast freezing is carried out such that the product reaches a core temperature within the range of between −15° and −50° C.

6. The process according to claim 1, further comprising storing the frozen product in an inert gas atmosphere prior to freeze-drying the frozen product.

7. The process according to claim 6, wherein the intermediate storage is carried out at a temperature within the range of between −15° and −50° C.

8. The process of claim 1, wherein the freeze drying is carried out at a pressure within the range of about 0.1 to about 50 mbar and a temperature such that the product temperature does not exceed about 45° C.

* * * * *